United States Patent
Jasra et al.

(10) Patent No.: US 10,391,468 B2
(45) Date of Patent: Aug. 27, 2019

(54) HALOGENATION OF HYDROCARBONS

(71) Applicant: RELIANCE INDUSTRIES LIMITED, Mumbai (IN)

(72) Inventors: Rakshvir Jasra, Gujurat (IN); Ninad Deepak Ingle, Pune (IN); Pradeep Paresh Kapadia, Mumbai (IN); Pradip Munshi, Gujarat (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 124 days.

(21) Appl. No.: 14/689,211

(22) Filed: Apr. 17, 2015

(65) Prior Publication Data

US 2016/0008786 A1    Jan. 14, 2016

Related U.S. Application Data

(63) Continuation of application No. PCT/IN2013/000633, filed on Oct. 18, 2013.

(30) Foreign Application Priority Data

Oct. 18, 2012   (IN) .......................... 3049/MUM/2012

(51) Int. Cl.
*B01J 19/12* (2006.01)
*C07C 17/10* (2006.01)
(Continued)

(52) U.S. Cl.
CPC ........... *B01J 19/127* (2013.01); *B01J 19/121* (2013.01); *B01J 19/18* (2013.01); *C07C 17/10* (2013.01);
(Continued)

(58) Field of Classification Search
CPC ............................ B01J 19/127; B01J 19/121; B01J 2219/1203; B01J 19/18; C07C 17/10;
(Continued)

(56) References Cited

U.S. PATENT DOCUMENTS

| | | | |
|---|---|---|---|
| 3,362,896 A | 1/1968 | Bier et al. | |
| 3,948,741 A * | 4/1976 | McCoy | ................... C07C 17/10 204/158.12 |

(Continued)

FOREIGN PATENT DOCUMENTS

| | | |
|---|---|---|
| GB | 1202229 A | 8/1970 |
| WO | WO-2013069542 A1 | 5/2013 |

OTHER PUBLICATIONS

International Search Report regarding Application No. PCT/IN2013/000633, dated Apr. 1, 2014.
(Continued)

*Primary Examiner* — Nicholas A Smith
*Assistant Examiner* — Colleen M Raphael
(74) *Attorney, Agent, or Firm* — Harness, Dickey & Pierce, P.L.C.

(57) ABSTRACT

The present disclosure relates to a process for the halogenation of hydrocarbon. In accordance with the process of the present disclosure a hydrocarbon and a halogen is introduced in a reaction vessel. Light having wavelength in the range of 390 to 780 nm is then passed into the reaction vessel for a time period of 2 to 12 hrs. to obtain a halogenated hydrocarbon. The hydrocarbon is agitated before or after the introduction of the halogen in to the reaction vessel.

6 Claims, 3 Drawing Sheets

(51) Int. Cl.
B01J 19/18 (2006.01)
C08F 8/22 (2006.01)
C08C 19/14 (2006.01)
C07C 17/14 (2006.01)
C08F 136/06 (2006.01)

(52) U.S. Cl.
CPC .............. *C07C 17/14* (2013.01); *C08C 19/14* (2013.01); *C08F 8/22* (2013.01); *C08F 136/06* (2013.01); *B01J 2219/1203* (2013.01)

(58) Field of Classification Search
CPC .......... C07C 17/14; C08F 136/06; C08F 8/22; C08C 19/14
USPC ... 204/158.1, 157.94–157.95, 157.79, 157.8, 204/157.84, 157.86, 157.98–158.12
See application file for complete search history.

(56) References Cited

U.S. PATENT DOCUMENTS

| 4,029,862 | A | * | 6/1977 | Liu | C08F 8/22 525/334.1 |
| 4,049,517 | A | | 9/1977 | Adachi et al. | |
| 4,102,760 | A | | 7/1978 | Robinson et al. | |
| 4,423,263 | A | * | 12/1983 | Minisci | C07C 17/14 570/197 |
| 6,590,041 | B1 | * | 7/2003 | Eguchi | C08F 8/20 525/331.6 |
| 2004/0048945 | A1 | * | 3/2004 | Ueshima | C08F 8/22 522/114 |
| 2004/0116755 | A1 | * | 6/2004 | Stanger | C07B 39/00 570/257 |
| 2005/0087434 | A1 | * | 4/2005 | Tarancon | B01J 19/123 204/158.21 |
| 2014/0309325 | A1 | * | 10/2014 | Inaoka | C08F 8/22 522/132 |
| 2017/0051081 | A1 | * | 2/2017 | Munshi | B01J 19/18 |

OTHER PUBLICATIONS

Yuta Nishina et al. "Bromination of hydrocarbons with CBr4, initiated by light-emitting diode irradiation." Beilstein Journal of Organic Chemisty. vol. 9. pp. 1663-1667. Aug. 14, 2013.

Revised International Search Report regarding Application No. PCT/IN2013/000633, dated Apr. 1, 2014.

* cited by examiner

HALOGENATION OF HYDROCARBONS

CROSS-REFERENCE TO RELATED APPLICATIONS

This application is a continuation of International Application No. PCT/IN2013/000633, filed Oct. 18, 2013. This application claims priority to Indian Application No. 3049/MUM/2012, filed Oct. 18, 2012. The disclosures of the above applications are incorporated herein by reference.

FIELD OF THE DISCLOSURE

The present invention relates to halogenation of hydrocarbons.

BACKGROUND

Halogenation of hydrocarbons is typically carried out either in the vapor phase or in the liquid phase. The vapor phase halogenation of hydrocarbons is a rapid reaction. However, it is observed that vapor phase reactions are highly exothermic and therefore need extreme care and control.

In contrast, liquid phase halogenation of hydrocarbons is safe but the rate of halogenation of hydrocarbons is usually quite low, which further necessitates the use of catalysts for accelerating the rate of reaction. The catalysts generally used for liquid phase halogenation of hydrocarbons include metallic chlorides and iodine. However, such catalysts inevitably cause severe environmental concerns such as discharged waste liquids, gases and the like.

To counter these environmental concerns, efforts have been made to use ultra violet radiation as a catalyst.

For instance, U.S. Pat. No. 4,102,760 discloses a method of chlorinating vinylidene fluoride polymer resin in the presence of an initiator compound, triethanolamine and ultraviolet radiation. U.S. Pat. No. 4,102,760 utilizes a quartz mercury vapor lamp having a minimum intensity of 450 watts which emits about 28% of its energy in the ultraviolet region as a source of ultraviolet light. Further, a water-jacketed quartz immersion well is used to separate the reaction medium from the quartz mercury vapor lamp.

U.S. Pat. No. 3,362,896 discloses a process for the chlorination of vinyl chloride polymers in liquid suspension through irradiation with visible or short wavelength light. The light source used in accordance with the U.S. Pat. No. 3,362,896 is a vapor/gas-based, high pressure mercury lamp.

GB1202229 discloses a process the preparation of chlorinated polyvinyl chloride wherein 100 W mercury lamp is used as a light source.

WO2013069542 discloses a process for producing a chlorinated vinyl chloride resin. The process includes chlorination of a vinyl chloride resin by irradiating with ultraviolet light. The ultraviolet light source used in accordance with WO2013069542 includes ultraviolet LED, an organic EL, an inorganic EL and an ultraviolet laser.

The filament-based or vapor/gas-based lamp used in the prior art as a source of UV light emits defused or multi-directional UV light that exhibits a high rate of intensity decay with distance. Accordingly, these lamps are incapable of inducing effective reactions which further lead to consumption of high amount of electrical power. Additionally, these lamps are bulky and have a short life period (8000-15000 hours).

Further, the use of such light sources may cause short and long term health hazards by way of UV radiations scattered in the immediate environment. Furthermore, reaction vessels made of quartz make the halogenation process and its apparatus expensive.

Thus, there is a need for a novel and economic process for halogenation of hydrocarbons. Further, there is also a need for an apparatus which will utilize low-intensity solid state lights for halogenation of hydrocarbons.

OBJECTS

Some of the objects of the system of the present disclosure, which at least one embodiment discussed herein satisfies, are as follows:

It is an object of the present disclosure to ameliorate one or more problems of the state-of-the-art or at least provide a useful alternative.

It is an object of the present disclosure to provide a process for halogenation of hydrocarbons which is economic.

It is another object of the present disclosure to provide a process for halogenation of hydrocarbons which is environmentally safe.

It is a still another object of the present disclosure to provide a process for halogenation of hydrocarbons which utilizes light emitting devices.

It is a still another object of the present invention to provide a process for halogenations of hydrocarbons utilizing solid state light emitting devices.

It is a still another object of the present invention to provide a process for halogenations of hydrocarbons without addition of an additive like swelling agent, inititor dispersing agents.

It is a further object of the present disclosure to provide an apparatus for halogenation of hydrocarbons.

It is still a further object of the present disclosure to provide an apparatus for halogenation of hydrocarbons which is energy efficient and economic.

It is even a further object of the present disclosure to provide an apparatus for halogenation of hydrocarbons which is easy to handle.

SUMMARY

In accordance with one aspect of the present disclosure there is provided a process for halogenation of a hydrocarbon; said process comprising the following steps:
  i. introducing the hydrocarbon in a reaction vessel;
  ii. introducing a halogen in the reaction vessel; and
  iii. passing light of wavelength in the range of 390 to 780 nm emitted by a plurality of solid state light emitting devices, into the reaction vessel for a predetermined time period to obtain a halogenated hydrocarbon,
wherein, the hydrocarbon is agitated before or after the method step of introducing the halogen in to the reaction vessel; and
wherein, said process is carried out in an inert atmosphere.

Typically, the hydrocarbon is introduced in the reaction vessel in the form of a slurry or a solution.

Typically, the hydrocarbon is agitated with the help of a rotating stirrer at speeds ranging from 200 to 850 rpm for a time period of 5 to 60 minutes.

Typically, the light is passed into the reaction vessel for a time period of 2 to 12 hrs.

Typically, the solid state light emitting device is at least one selected from the group consisting of Light Emitting Diodes (LEDs), LASER, Organic Electroluminescence material, Inorganic Electroluminescence, Organic Light Emitting Diodes and Inorganic Light emitting Diodes.

Typically, the light source from which light is passed is a bank of solid state light emitting devices placed on at least one location selected from the group consisting of outside the reaction vessel, inside the reaction vessel and embedded on the walls of the reaction vessel.

Typically, the solid state devices are placed outside the reaction vessel at a distance of 0.2 to 12 cm from the exterior wall of the reaction vessel, preferably at a distance of 0.5 to 4 cm.

Typically, the step of passing light from a bank of solid state light emitting devices includes guiding the beam of light to a reaction zone of the reaction vessel in which the process is taking place.

The process of the present disclosure further comprises the step of heating the hydrocarbon at a temperature in the range of 40 to 90° C. before executing step (ii).

Typically, the hydrocarbon is at least one selected from the group consisting of a compound comprising at least one C—H group, polymers, aliphatic hydrocarbons and aromatic hydrocarbons.

Typically, the hydrocarbon is at least one polymer selected from the group consisting of Polyvinyl Chloride, polyolefin, polyester and a rubber compound.

Typically, the hydrocarbon is Polyvinyl Chloride and the process involves efficient halogenation of Polyvinyl Chloride.

Typically, the halogen is selected from chlorine, bromine, and halogenated compounds liberating radical of chlorine or bromine upon light irradiation by solid state light emitting devices.

In accordance with another aspect of the present disclosure there is provided an apparatus for halogenation of a hydrocarbon, said apparatus comprising a reaction vessel, purging means to purge fluid into said reaction vessel, a centrally mounted stirrer and a bank of solid state light emitting devices.

The apparatus of the present disclosure includes guiding means to guide the light from the solid state light emitting devices to a reaction zone of the reaction vessel.

Typically, the solid state light emitting device is at least one selected from the group consisting of LED, LASER, Organic Electroluminescence material, Inorganic Electroluminescence, Organic Light Emitting Diodes and Inorganic Light emitting Diodes.

Typically, a light source from which the light having wavelength of 390 to 780 nm is passed, is a bank of solid state light emitting devices placed on at least one location selected from the group consisting of outside the reaction vessel, inside the reaction vessel and embedded on the walls of the reaction vessel.

Typically, the bank of solid state light emitting devices is placed at a distance of 0.2 to 12 cm from the exterior wall of the reaction vessel, preferably at a distance of 0.5 to 4 cm.

Typically, the reaction vessel is glass walled and transparent.

BRIEF DESCRIPTION OF DRAWINGS

The process for halogenation of hydrocarbons of the present disclosure will now be explained in relation to the accompanying non-limiting drawings, in which.

DETAILED DESCRIPTION

Figure 1:
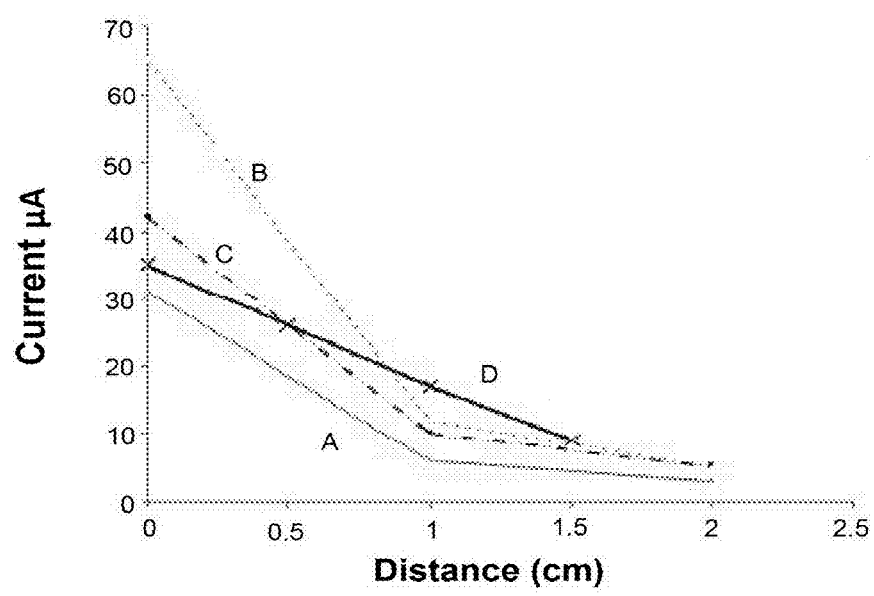
FIG. 1 illustrates a graphical representation depicting intensity decay pattern of light transmitted through the hydrocarbon slurry; wherein A represents the light transmitted through the slurry using 24 W Ultraviolet lamp emitting light of wavelength 254 nm; B represents the light transmitted through the slurry using 48 W Ultraviolet lamp emitting light of wavelength 254 nm; C represents the light transmitted through the slurry using 72 W Ultraviolet lamp emitting light of wavelength 254 nm and D represents the light transmitted through the slurry using 38 W LEDs emitting light of wavelength 410 nm.

In accordance with the present disclosure there is provided a process for halogenation of hydrocarbons. The process involves the following steps:

In the first step, a hydrocarbon is introduced into a reaction vessel. Non limiting examples for hydrocarbons used in accordance with the present disclosure include polymers, aliphatic hydrocarbons and aromatic hydrocarbons. In addition, hydrocarbon includes but is not limited to compound consisting at least one C—H group, Polyvinyl Chloride, polyolefin, polyester and rubber compounds.

Further, in accordance with one embodiment of the present disclosure hydrocarbon is in the form of a slurry or a solution In the second step, a halogen is introduced in to the reaction vessel. The halogen used in accordance with the present disclosure is in at least one form selected from the group consisting of liquid form, solid form and gaseous form. Non limiting examples of halogen includes fluorine, chlorine, bromine, iodine or any halogenated compounds that creates halogenated free radical upon irradiation by light emitted through solid state light emitting device.

In accordance with one embodiment of the present disclosure, the hydrocarbon is first agitated at a speed ranging from 200 to 850 rpm for a period of 5 to 60 minutes and then the halogen is introduced into the reaction vessel. Alternatively, the hydrocarbon is first mixed with the halogen to obtain a mixture and then the mixture is agitated at a speed ranging from 200 to 850 rpm for a period of 5 to 60 minutes.

In accordance with another embodiment of the present disclosure the hydrocarbon is heated at a temperature of 40 to 90° C. before the introduction of halogen into the reaction vessel.

In the third step, light is passed into the reaction vessel for a period of 2 to 12 hrs. to obtain a halogenated hydrocarbon. The light source, from which light of wavelength 390 to 780 nm preferably 390 to 493 nm is passed, is a bank of solid state light emitting devices. The distance between the exterior wall of the reaction vessel and the bank of solid state light emitting devices placed outside the reaction vessel is in the range of 0.2 to 12 cm. The bank of solid state light emitting devices placed on at least one location selected from the group consisting of outside the reaction vessel, inside the reaction vessel and embedded on the walls of the reaction vessel.

The solid state light emitting devices used as a light source in accordance with the present disclosure includes but is not limited to LED, LASER, Organic Electroluminescence material, Inorganic Electroluminescence, Organic Light Emitting Diodes and Inorganic Light emitting Diodes.

The step of passing light from a bank of solid state light emitting devices further includes guiding the beam of light to a reaction zone in the reaction vessel in which the process of halogenation of hydrocarbon is taking place.

The process of halogenation of hydrocarbon is carried out in an inert atmosphere established by purging an inert gas. In accordance with one embodiment, nitrogen gas is passed into the reaction vessel to establish the inert atmosphere.

In accordance with one of the embodiments of the present disclosure the hydrocarbon is PVC and the process involves efficient halogenation of PVC.

In accordance with the present disclosure there is also provided an apparatus for halogenation of hydrocarbons. The apparatus includes a reaction vessel, purging means to purge fluid into the reaction vessel, a centrally mounted stirrer and a bank of solid state light emitting devices adapted to generate light having wavelength in the range of 390 to 780 nm, preferably 390 to 493 nm. The bank of solid state light emitting devices placed on at least one location selected from the group consisting of outside the reaction vessel, inside the reaction vessel and embedded on the walls of the reaction vessel. The distance between the exterior wall of the reaction vessel and the bank of solid state light emitting devices place outside the reaction vessel is in the range of 0.2 to 12 cm.

The apparatus of the present discloser also includes guiding means to guide the light from the bank of solid state light emitting devices to a reaction zone of the reaction vessel. The guiding means includes but is not limited to waveguide, lens and set of lenses.

Typically, the reaction vessel is glass walled and transparent.

When UV light emitted by three different types of gas phase lamps, namely lamp 1, lamp 2 and lamp 3 is irradiated on hydrocarbon an exponential decay in the intensity of the transmitted light is observed, while linear decay in the transmitted light is observed when the light emitted by the LEDs of the present disclosure is used (FIG. 1).

Figure 2:
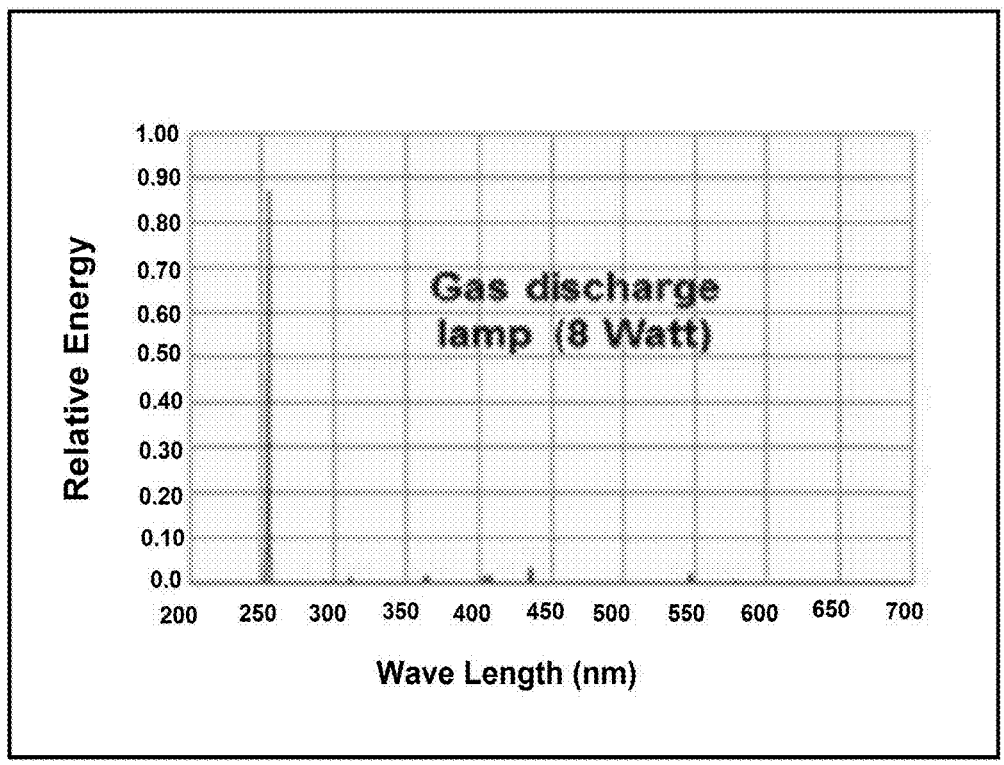
FIG. 2 illustrates the relative intensity of light emitted by a gas-based lamp.
Figure 3:
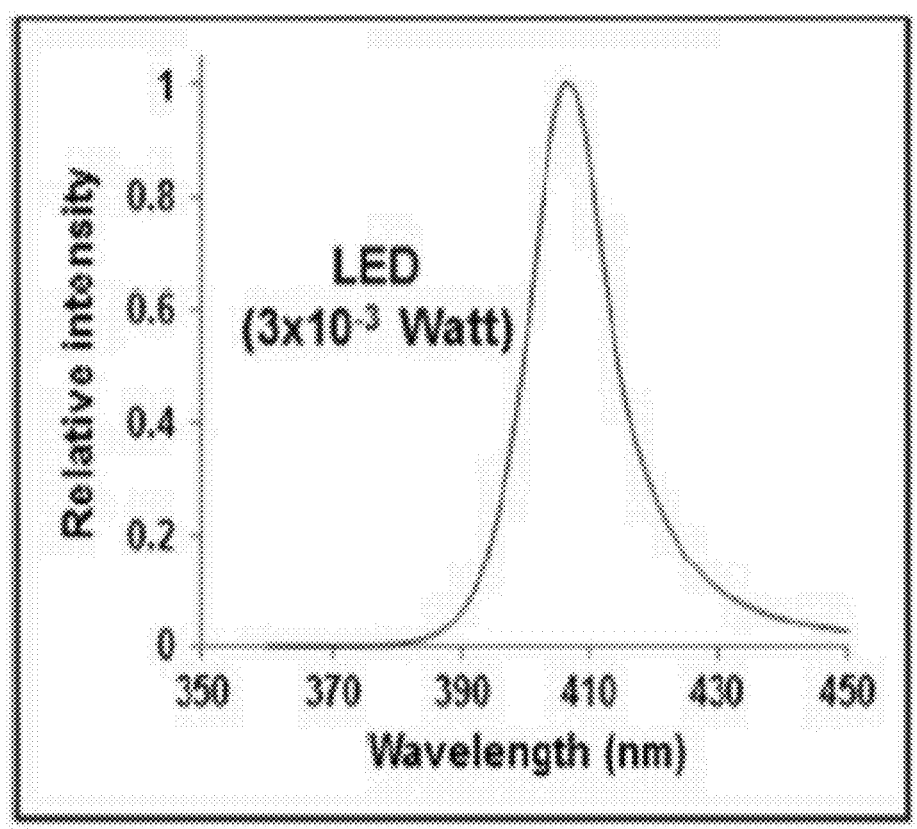
FIG. 3 illustrates the relative intensity of light emitted by the LEDs used in the apparatus of the present disclosure.

Further, in view of FIG. 2 and FIG. 3, it is evident that the relative intensity of the light emitted by the conventional gas-based lamp is less than the relative intensity of LEDs of the present disclosure. Thus LEDs reduce wastage of energy, as the light intensity is directly proportional to the input current.

Based on the foregoing observations, the present disclosure provides an economic, energy efficient and environmental friendly process, and an apparatus for halogenation of hydrocarbons that exhibit huge electrical power saving by replacing conventional filament-based or vapor/gas-based lamps with LEDs.

Hereinafter, the present disclosure will be described in more detail with reference to the following examples, but the scope of the present disclosure is not limited thereto.

EXAMPLE 1

Halogenation of a Halo-hydrocarbon Polymer 1010 grams (g) of aqueous slurry of poly vinyl chloride (PVC) containing 160 g of PVC was taken in a reaction vessel (reactor). Subsequently, the slurry was agitated at a speed of 200 revolutions per minute (rpm) for an initial time period of 5 minutes while nitrogen gas was purged inside the reaction vessel through the slurry. The speed of rotation was then increased to 650 rpm and nitrogen purging was continued for another 40 minutes for removing air or oxygen from the reaction vessel and the slurry. Temperature was brought to 70° C. under inert atmosphere while agitation was on. Subsequently, purging of nitrogen was stopped and chlorine was then purged through the slurry maintaining the same conditions. One or more light emitting devices (LEDs) were switched on when the reaction vessel and the slurry were found to be saturated with chlorine. The start time of the reaction was noted from the time at which the mixture was exposed to the LED light. The temperature was maintained at 70° C. before switching off one or more light emitting devices. After 6 hours of exposure to LED light, the reaction was stopped by stopping the purging of chlorine. Subsequently, nitrogen gas was purged for 1 hour to expel out unreacted chlorine gas from reaction system and reaction mass. Chlorinated polyvinylchloride (CPVC) was obtained in aqueous slurry that was filtered and washed with 1500 milliliter (ml) of water in three parts under reduced pressure to obtain a wet cake product. The wet cake was then dried at 70° C. under blow of air and CPVC was specifically obtained as a white dry powder. Chlorine content (by weight) was checked by weight increase with respect to the PVC dry powder. CPVC so obtained contains 67% of chlorine by weight. Table 1 illustrates reaction time for 67% chlorination of hydrocarbon using different wavelengths.

TABLE 1 chlorination of hydrocarbon using light at different wavelengths:

| No | Wavelength (nm) | Reaction time hr. |
|---|---|---|
| 1 | 395 | 6 |
| 2 | 410 | 5 |
| 3 | 450 | 4.5 |

EXAMPLE 2

Halogenation of a Pure Hydrocarbon Polymer 50 g of polyethylene was taken in a reaction vessel (reactor). 850 ml of water was added to the polymer to form slurry. Subsequently, the slurry was agitated at a speed of 500 rpm for an initial time period of 5 minutes while nitrogen gas was purged inside the reaction vessel through the slurry. Nitrogen purging was continued for another 40 minutes for removing air or oxygen from the reaction vessel and the slurry. Subsequently, purging of nitrogen was stopped and chlorine was then purged through the slurry maintaining the same conditions. The temperature of the slurry was set to 50° C. One or more light emitting devices were then switched on when the reaction vessel and the slurry, were found to be saturated with chlorine. The start time of the reaction was noted from the time at which the mixture was exposed to the LED light having wavelength of 405 nm. After 3 hours of exposure to the LED light, the reaction was stopped by stopping the purging of chlorine. Subsequently, nitrogen gas was purged for 1 hour. Chlorinated polyethylene (CPE) was obtained in the form of a wet cake product in an aqueous slurry that was filtered and washed with 1000 ml of water in three parts under reduced pressure. The wet cake was then dried at 70° C. under blow of air and CPE was specifically obtained as a white dry powder. Chlorination of CPE was confirmed by oxygen flask test method followed by argento metric titration.

EXAMPLE 3

Halogenation of an Unsaturated Hydrocarbon Polymer 30 g of poly-butadiene rubber was taken in a reaction vessel (reactor). 800 ml of water was added to the polymer to form slurry. Subsequently, the slurry was agitated at a speed of 600 rpm for an initial time period of 5 minutes while nitrogen gas was purged inside the reaction vessel through the slurry. Nitrogen gas purging was continued for another 40 minutes for removing air or oxygen from the reaction vessel and the slurry. Subsequently, purging of nitrogen was stopped and chlorine was then purged through the slurry maintaining same conditions. The temperature of the slurry was set to 60° C. One or more light emitting devices were then switched on when the reaction vessel and the slurry were found to be saturated with chlorine. Start time of the reaction was noted from the time at which the mixture was exposed to the LED light. After 3 hours of exposure to the LED light having wavelength of 405 nm, the reaction was stopped by stopping the purging of chlorine. Subsequently, nitrogen was purged for 1 hour. Chlorinated poly-butadiene rubber (CPBR) was obtained in an aqueous slurry that was filtered and washed with 1000 ml of water in three parts under reduced pressure. The wet product was then dried at 60° C. under a blow of air and CPBR was obtained. Chlorination of CPBR was confirmed by oxygen flask method followed by argentometric test.

EXAMPLE 4

Halogenation of an Aliphatic Hydrocarbon 31 g (10 ml) liquid bromine and 25 ml of n-hexane were taken in a 100 ml round bottomed flask. The mixture was continuously stirred using a magnetic bar over a magnetic stirrer under room temperature. Nitrogen gas was then purged in to the round bottom flask for removing air or oxygen. The flask was exposed to the light emitted by one or more light emitting devices under room temperature. The start time of reaction was noted from the time the mixture was exposed to the LED light having wavelength of 405 nm. At the end of 5 hours, gas chromatography of reaction product depicted formation of brominated hexane.

EXAMPLE 5

Halogenation of an Aromatic Hydrocarbon 2 ml of toluene, and 2.26 ml of sodium bromide were taken in a round bottom flask. The mixture was continuously stirred using a magnetic stirrer. Nitrogen gas was then purged in to the round bottom flask for removing air or oxygen. Then 3.4 ml of 30% hydrogen peroxide solution was added to the mixture. The flask was exposed to the light emitted by one or more light emitting devices under room temperature. The start time of the reaction was noted from the time the mixture was exposed to the LED light having wavelength of 405 nm. At the end of 5 hours, analysis of the reaction mixture confirmed the formation of benzyl bromide.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The invention claimed is:

1. A process for halogenation of a hydrocarbon; said process comprising the following steps:
   i. introducing the hydrocarbon in a reaction vessel;
   ii. initially agitating the hydrocarbon in said reaction vessel at a speed of 200 rpm with a centrally mounted stirrer in said reaction vessel for an initial time period of 5 minutes;
   iii. increasing said speed of 200 rpm to a speed of 650 rpm and stirring the hydrocarbon at said speed of 650 rpm with said centrally mounted stirrer in said reaction vessel for a time period of 40 minutes;
   iv. introducing a halogen in the reaction vessel while stirring the hydrocarbon at said speed of 650 rpm with said centrally mounted stirrer in said reaction vessel for said time period of 40 minutes; and
   v. passing light of wavelength in the range of 390 to 780 nm emitted by a plurality of solid state light emitting devices placed outside said reaction vessel at a distance of 0.5 to 4 cm from the exterior wall of said reaction vessel, into said reaction vessel for a period of time to obtain a halogenated hydrocarbon,
   wherein, said process steps of (ii) and (iii) are carried out in an inert atmosphere.

2. The process as claimed in claim 1, wherein the light is passed into the reaction vessel for a time period of 2 to 12 hrs.

3. The process as claimed in claim 1, further comprises the step of heating the hydrocarbon in said reaction vessel at a temperature in the range of 40 to 90° C. before executing step (iv).

4. The process as claimed in claim 1, wherein the hydrocarbon is at least one selected from the group consisting of a compound comprising at least one C—H group, aliphatic hydrocarbons and aromatic hydrocarbons.

5. The process as claimed in claim 1, wherein the hydrocarbon is Polyvinyl Chloride and the process involves efficient halogenation of Polyvinyl Chloride.

6. The process as claimed in claim 1, wherein the halogen is selected from chlorine, bromine, and halogenated compounds liberating radical of chlorine or bromine upon light irradiation by solid state light emitting devices.

* * * * *